US007002059B1

(12) United States Patent
Burrell et al.

(10) Patent No.: US 7,002,059 B1
(45) Date of Patent: Feb. 21, 2006

(54) MODIFICATION OF PLANT FIBERS

(75) Inventors: Michael Meyrick Burrell, Cambridge (GB); Amanda Pat Cambridge, York (GB); Martin Jack Maunders, Cambridge (GB); Simon McQueen-Mason, York (GB)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 09/383,579

(22) Filed: Aug. 25, 1999

(30) Foreign Application Priority Data

Aug. 29, 1998 (GB) .................................... 9818808

(51) Int. Cl.
*C12N 15/82* (2006.01)
*C12N 15/87* (2006.01)
*A01H 5/00* (2006.01)
*A01H 5/10* (2006.01)

(52) U.S. Cl. ...................... 800/298; 800/278; 800/290; 800/319; 435/468

(58) Field of Classification Search ................ 800/278, 800/290, 298, 287, 319; 536/23.1, 23.6; 435/468

See application file for complete search history.

(56) References Cited

U.S. PATENT DOCUMENTS 5,597,718 A * 1/1997 John et al. ................... 800/263

FOREIGN PATENT DOCUMENTS

| EP | 0465572 | 1/1992 |
| EP | 0647715 | 4/1995 |

OTHER PUBLICATIONS

Bowie et al, Science 247:1306-1310, 1990.*
McConnell et al, Nature 411 (6838):709-713, 2001.*
Choi et al (2003, The Plant Cell 15:1386-1398).*
Lee et al (2003, Plant Physiology 131:985-997).*
Merriam-Webster OnLine, 2004, WWW.M-W.com.*
Bamber, Appita 38:210-216 (1995).
Bevan, Nucl. Acids Res. 12:8711-1872 (1984).
Boudet et al., New Phytol. 129:203-236 (1995).
Carpita et al., Plant J. 3:1-30 (1993).
Cho et al., Plant Physiol. 113:1137-1143 (1997).
Cho et al., Plant Physiol. 113:1145-1151 (1997).
Cosgrove, New Phytol. 124:1-23 (1993).
Cosgrove, BioEssays 18:533-540 (1996).
Cosgrove et al., Proc. Nat. Acad. Sci. USA 94:6559-6564 (1997).
Dablaere et al., Nucl. Acids Res. 13:4777-4788 (1985).
Denecke et al., EMBO J. 11:2345-2355 (1992).
Figurski et al., Proc. Natl. Acad. Sci USA, 76:1648-1652 (1979).
Grima-Pattenati et al., Plant Mol. Biol. 21:1085-1095 (1993).
Hawkins et al., Plant Physiol. 104:75-84 (1994).
Herrera-Estrella et al., EMBO J, 2:987-995 (1983).
Hibino et al., Plant Physiol. 104:305-306 (1994).
Hood et al., Transgenic Res. 2:208-218 (1993).
Horsch et al., Science 227:1229-1231 (1985).
Keller et al., Plant J. 8:795-802 (1995).
Li et al., Planta 191:349-356 (1993).
McQueen-Mason, J. Exp. Bol. 48:1639-1650 (1995).
McQueen-Mason et al., Plant Physiol. 102:122 (1993) (abstr. No. 691).
McQueen-Mason et al., Proc. Natl. Acad. Sci USA, 91: 6574-6578 (1994).
McQueen-Mason et al., Plant Physiol. 107:87-100 (1995).
McQueen-Mason et al., Plant Cell 4:1425-1433 (1992).
Miki et al., Plant Physiology, Biochemistry and Molecular Biology, $1^{st}$ edn., Dennis and Turpin, eds., Longman Scientific & Technical Publishers, UK, pp. 473-489 (1990).
Poeydomenge et al., Plant Physiol. 105:749-750 (1994).
Seth, Tappi J. 78:99-102 (1995).
Shcherban et al., Proc. Natl. Acad. Sci. USA 92:9245-9249 (1995).
Vannacanneyt et al., Mol. Gen. Genet. 220:245-250 (1990).
Verhaegen et al., Genome 39:1051-1061 (1996).
Walden, Plant Biochemistry and Molecular Biology, $1^{st}$ edn., Lea and Leegood, eds., John Wiley & Sons Ltd., London, pp. 275-295 (1994).
Weising et al., Annu. Rev. Genet. 22:421-477 (1988).
Pawlowski et al., Isolation of total, poly(A) and polysomal RNA from plant tissues, Kiuwer Academic Publishers, Belgium (1994).
Ranatunga MS, Ceyton For 6:101-112 (1964).
Verwoerd et al., Nucl. Acids Res. 17:2362 (1989).
Stewart et al., *"Spectroscopic Analysis of Plant Cell Walls"* Scottish Crop Research Institute Annual Report 1994, pp. 103-108, Editors: D.A. Perry and T.D. Heilbronn, ©Scottish Crop Research Institute 1995.

* cited by examiner

*Primary Examiner*—Amy J. Nelson
*Assistant Examiner*—Stuart F. Baum
(74) *Attorney, Agent, or Firm*—Kenyon & Kenyon

(57) ABSTRACT

The invention relates to the isolation and characterisation of novel expansin gene sequences from heterologous and homologous tree species and re-introducing such novel genes into trees so as to alter expansin levels. Six novel genes have been identified. *Eucalyptus* has also been transformed using the cucumber EX29 sequence (GenBank, Accession No. U30382-known as Cs-EXP1) (SEQ. ID. NO: 9). A change in the plant height and internode length was observed compared with control plants.

7 Claims, 2 Drawing Sheets

MODIFICATION OF PLANT FIBERS

Figure 1A:
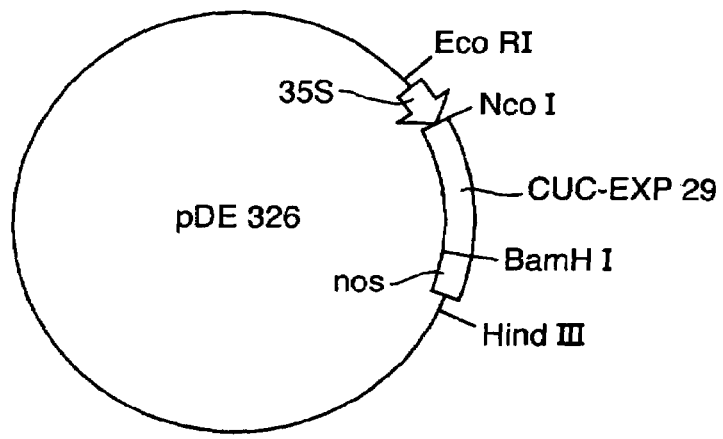

This invention relates to the modification of the morphology of plant fibre cells. The invention is exemplified by methods of using genetic constructs for the modification of, in particular, but not exclusively, *Eucalyptus* fibres, for example.

The primary product of the forestry industry is considered to be wood, although more fundamentally it could be defined as fibre. The industry supplies a wide range of feedstocks to the solid wood and pulp/paper industries who produce a multiplicity of products. The forester must therefore seek to cater for the competing needs of these industries, and even within the individual industries, there is a range of different requirements. For example, different paper grades require different qualities in the starting material.

Forestry-based operations depend upon a balance between the capability of the forester to supply the processor with fibre having specific properties, and the ability of the processor to modify his process and so accommodate the available feedstock. The design and operation of processing plants are influenced by the wood (fibre) properties of the feedstock.

Notwithstanding these specific demands, fibre uniformity and strength are common requirements for most industrial uses, and hence the fibre supplied by the forester must be capable of delivering these properties to the processor.

In pulp manufacture, for example, strength characteristics are determined in part by fibre length. Increased fibre length leads to the production of paper with increased strength. Bond strength is attributed to contact between the fibres and the adhesion capabilities of the surfaces, which are dependent upon fibre length, perimeter and coarseness. Also, during the manufacturing process, increased fibre length increases the strength of wet webs enabling easier handling (Seth, 1995).

However, long fibres are not desirable for all applications. In some cases, shorter fibres are preferable, such as in the production of smooth-surfaced papers.

Fibre properties differ between species, and consequently particular species have been limited historically to particular applications. Fibres from hardwood species are generally much shorter than those from softwoods. This results in the production of pulp and paper with desirable surface characteristics such as smoothness and brightness, but with low strength characteristics. In practice, where a single species providing fibre with an appropriate combination of characteristics has not been available, the mixing of long and short fibres from different species is used. If a single source were available, possessing the desirable characteristics plus optimal fibre length, this would be of great benefit to the processor. Some common species and their fibre lengths are exemplified in Table 1 below.

TABLE 1

Fibre Lengths of Various Tree Species

| Species | Fibre Length (mm) |
| --- | --- |
| Loblolly Pine | 3.5–4.5 |
| Western Hemlock, Western Spruce | 2.5–4.2 |
| Southern Hardwood | 1.2–1.4 |
| Northern Hardwood | 1.0–1.2 |
| Eucalyptus | 0.8–1.0 |
| White Oak | 0.59 |
| Sweetgum | 0.48 |
| Aspen | 0.35 |

*Eucalyptus* trees represent the largest sources of fibres used globally in the paper industry (Bamber 1985; Ranatunga, 1964), and world-wide, there are an estimated ten to fifteen million hectares of land planted with *Eucalyptus* (Verhaegen and Plomion 1996). The major advantage of Eucalypts is their very high growth rates and ability to grow in a wide range of conditions, both tropical and temperate.

However, *Eucalyptus* fibres are significantly shorter than those from other, once more popular, sources of fibre such as pine. Thus papers that are made from *Eucalyptus* pulp are often weak and usually require reinforcement with longer fibres from other sources increasing the production costs. If trees could be produced with longer fibres, this would be a considerable advantage to the paper industry, increasing the quality of the raw materials for pulp and paper synthesis.

Through tree breeding it is possible to achieve some modification of fibre characteristics. For example, interspecific triploid hybrids of poplar have been developed which have longer fibres than the parental species.

Genetic variation in fibre properties is also evident within species. Fibre characteristics are controlled by a complex set of genetic factors and are not easily amenable to classical breeding methods. Therefore, existing genetic variation has not been exploited significantly in tree breeding programmes. Whilst knowledge is now being accumulated on the heritability of wood properties, previously these were not often considered as important as growth characteristics and were sometimes sacrificed in pursuit of the latter. In some instances, growth rate is negatively correlated with fibre characteristics, though this does not always hold true (e.g. in Eucalypts), and breeding efforts are now being made to capture the benefits of both.

In many cases fibre properties are sufficient for the end product, and improvement is considered unnecessary. For example, increasing fibre length beyond 2 mm causes little increase in tear strength or tensile strength, and many softwood fibres are commonly around 3 mm long, i.e. greater than the minimum for desired strength. However, fibres in juvenile wood tend to be shorter and there is an increased usage of juvenile material through a reduction in rotation times. Hence, there is scope for improvement even in those species which commonly yield long fibres.

From the perspective of the pulp and paper industry, fibres are specific types of plant cell walls that have been subjected to a range of treatments to remove all contents and most non-cellulosic wall components (Stewart et al, 1994). In woody plants the fibres are made up of dead cell wall material. In order to produce longer fibres it is necessary to have longer living cells during growth, before fibre formation.

The cell wall can be envisaged as a complex network of cellulose microfibrils linked together by noncovalent interactions with matrix polymers (Carpita and Gibeaut, 1993). The microfibrils are coated by a mixture of hemicelluloses which form extensive hydrogen-bonded interactions with the surface of the microfibrils. Coextensive with this is another network formed from various pectins which are held together largely by ionic linkages (McQueen-Mason, 1995).

To allow cells to grow and enlarge the wall components must loosen to enable slippage of the polysaccharides and proteins within the matrix (Cosgrove, 1993). Extension of the cell is then driven by the internal turgour pressure of the cell, which is considerable. The degree of extension during cell growth is controlled by the mechanical properties of the cell wall, which result from their composition and from the orientation of wall fibrils and structural polymers.

The control of cell wall extension is closely regulated by the plant to facilitate growth control and morphogenesis. The ultimate agents of control are enzymes located in the wall itself. If plants express cell wall "loosening" enzymes in their walls, then it seems likely that these enzymes can regulate cell growth. Altered levels of expression can thereby cause increased or reduced cell growth and fibre length. Changes in cell wall texture may also be produced.

One class of cell wall proteins are the Expansins. Expansins induce the extension of plant walls, and at present are the only proteins reported with demonstrated wall-loosening activity. Expansins were first isolated from cucumber hypocotyl cell walls by McQueen-Mason et al (1992) and characterised by their ability to catalyse wall loosening in an in vitro rheological assay.

The mode of action of expansins is believed to be by weakening the noncovalent bonding between the cellulose and hemi-cellulose, with the result that the polymers slide relative to one another in the cell wall (Cosgrove 1996). The precise biochemical action of expansins is unclear, although it is known that their effects are not due to exoglycanase or xylogucan endotransglycosylase activity (McQueen-Mason et al, 1992, McQueen-Mason & Cosgrove, 1993). Expansins appear to disrupt hydrogen bonding between cellulose microfibrils and hemicelluloses. The process enables wall loosening without any degradation of the polymers or an overall weakening of wall structure during expansion. Consistent with this mechanism, expansins have been shown to weaken cellulosic paper, which derives its mechanical strength from hydrogen bonding between cellulose fibres (McQueen-Mason and Cosgrove, 1994).

Expansins are able to restore the ability of isolated cell walls to extend in a pH dependent manner (McQueen-Mason and Cosgrove, 1995) and may be responsible for the phenomenon of "acid growth" in plants (Shcherban et al, 1995). Expansin proteins have been characterised in cucumber hypocotyls (McQueen-Mason et al, 1992), oat coleoptiles (Li et al, 1993), expanding tomato leaves (Keller and Cosgrove, 1995) and rice internodes (Cho and Kende, 1997).

Expansin cDNAs have been isolated and characterised from a number of plants and it is now evident that expansins exist as a multi-gene family showing a high level of conservation between species. cDNAs with high degrees of homology have been identified from collections of anonymous Expression Sequence Tag (EST) cDNAs from *Arabidopsis* and rice. These EST cDNAs exhibit a high degree of homology at the level of protein sequence (60–87%) indicating that expansin structure is highly conserved (Shcherban et al 1995). Expansins show no sequence similarity to other known enzymes, although they do have sequence similarities to some pollen allergens (Shcherban et al, 1995). Recently Cosgrove et al (1997) have shown that pollen allergens from maize also possess considerable expansin activity.

If plants can be modified to over-express expansins in their walls, then it would be expected that these plants will exhibit a marked increase in cell extension or growth. Conversely, a reduction in the expression of expansins should lead to a reduction in cell growth. It is therefore surprising that constitutive expression of expansin in eucalypts results in a reduction in height and internode length.

One approach to modifying the expression of expansins is via the introduction of recombinant DNA sequences into the plant genome. Several methods can be used to introduce foreign DNA into plant cells (see review by Weising et al, 1988; Miki and Iyer, 1990 and Walden 1994). *Agrobacterium tumefaciens*-mediated gene transfer is probably the most widely used and versatile of these methods (Walden, 1994).

Genetic modification experiments directed towards changing the wood and paper quality of trees has been investigated by other workers, particularly focusing on the lignin pathway in cells and lignin content in the final paper product (Hawkins and Boudet, 1994; Grima-Pettenati, et al, 1993; Poeydomenge et al, 1993; Boudet et al, 1995 and Hibino et al, 1994). The aim of the present invention differs in that it seeks to provide a means of controlling fibre growth and cell wall morphology.

An object of the present invention is to provide a method whereby trees can be modified to produce fibres of a desired length for specific applications. This will enable the forester to control the quality of his product. In addition it will enable the forester to produce a wide range of fibre types from a single or small number of species which can be selected as being ideally suited for cultivation in that particular site. This will result in both the economy of employing a single uniform silvicultural regime, and the flexibility of producing which ever type of fibre is required at a particular time.

The invention also provides a means of producing fibre of specific type from trees at particular periods in their growth cycle. For example, the production of long fibres from juvenile trees can be achieved, thereby accelerating the time to harvest of the crop.

This is achieved by firstly isolating and characterising expansin gene sequences from heterologous and homologous species and then reintroducing these genes into trees so as to alter expansin levels in the transgenic trees using the well known over-expression, co-suppression (described by DNAP in their European Patents Nos. 0465572 and 0647715) and anti-sense knockout strategies. This will lead to the cultivation of trees more suitable for paper production.

The present invention provides a nucleic acid coding sequence encoding a gene capable of modifying the extension of fibre cell walls, the nucleic acid coding sequence being one or more of SEQ. ID. Nos. 1–6 and 9 hereof.

The present invention also provides a method of transforming trees to modify the fibre characteristics in trees, the method comprising stably incorporating into the plant genome a chimaeric gene comprising a promoter and a nucleic acid coding sequence encoding a gene capable of modifying the extension of fibre cell walls, and regenerating a plant having an altered genome.

The present invention also provides trees having therein a chimaeric gene comprising a promoter and a nucleic acid coding sequence capable of modifying the extension of fibre cell walls.

The present invention also provides a chimaeric gene capable of modifying the extension of cell walls, said chimaeric gene comprising a promoter and a nucleic acid coding sequence encoding a gene capable of modifying the extension of fibre cell walls, said nucleic acid coding sequence being one or more of SEQ. ID. Nos. 1–6 or the cucumber Ex 29 coding sequence (SEQ. ID. No. 9), or a sequence which has sufficient homology to hybridise to any one of SEQ. ID. Nos. 1–6 or cucumber Ex 29 (SEQ. ID. No. 9) under medium stringency conditions.

Preferably the chimaeric gene further comprises a terminator.

Constructs having the DNA structural features described above and trees incorporating such constructs and/or chimaeric genes according to the invention are also aspects of the invention.

Plant cells containing chimaeric genes comprising a nucleic acid coding sequence capable of modifying the extension of fibre cell walls are also an aspect of this invention, as is the seed of the transformed plant containing chimaeric genes according to the invention.

The chimaeric gene may comprise the nucleic acid coding sequence as it exists in the genome, complete with endogenous promoter, terminator, introns and other regulatory sequences, or the nucleic acid coding sequence, with or without introns, may be combined with a heterologous promoter, terminator and/or other regulatory sequences.

The promoter may be a constitutive promoter, such as the cauliflower mosaic virus 35S promoter (CaMV35 S), the cauliflower mosaic virus 19S promoter (CaMV19S) or the nopaline synthase promoter, a tissue specific promoter, such as the rolC, patatin or petE promoters, or an inducible promoter, such as AlcR/AlcS. Other suitable promoters will be known to those skilled in the art.

The nucleic acid sequence, or parts thereof, may be arranged in the normal reading frame direction, i.e. sense, or in the reverse reading frame direction, i.e. antisense. Up or down regulation of the activity of the expansin protein or gene encoding therefor using sense, antisense or co-suppression technology may be used to achieve alteration in the length of fibre cell walls.

Preferably the nucleic acid sequence encodes one or more of the class of proteins known as expansins. More preferably the nucleic acid sequence is derived from *Eucalyptus* or cucumber.

The nucleic acid sequence may advantageously be one or more of SEQ. ID. Nos. 1–6 hereof. Alternatively, the nucleic acid sequence may be the cucumber expansin sequence cucumber Ex29 (SEQ. ID. No. 9; Genbank Accession No. U30382—known as Cs-EXP1). The sequence is also described in Shcheraban et al (1995).

Alternatively, the nucleic acid sequence may be a sequence which has sufficient homology to hybridise to any one of SEQ. ID. Nos. 1–6 or cucumber Ex29 (SEQ. ID. No. 9) under medium stringency conditions (washing at 2×SSC at 65° C.).

Preferably the nucleic acid sequence is an mRNA or cDNA sequence, although it may be genomic DNA.

Trees which may suitably be transformed using the inventive method include Eucalypts, Aspen, pine, larch.

The nucleic acid sequence may be introduced by any of the known genetic transformation techniques such as *Agrobacterium tumefaciens* mediated transformation, *Agrobacterium rhizogenes* mediated transformation, biolistics, electroporation, chemical poration, microinjection or silicon-fibre transformation, for example.

Figure 1B:
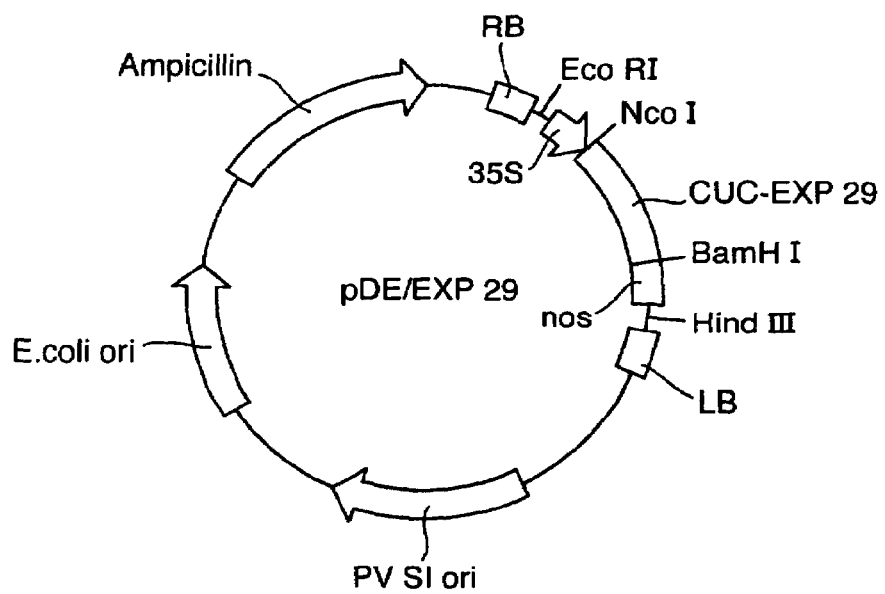
Figure 1C:
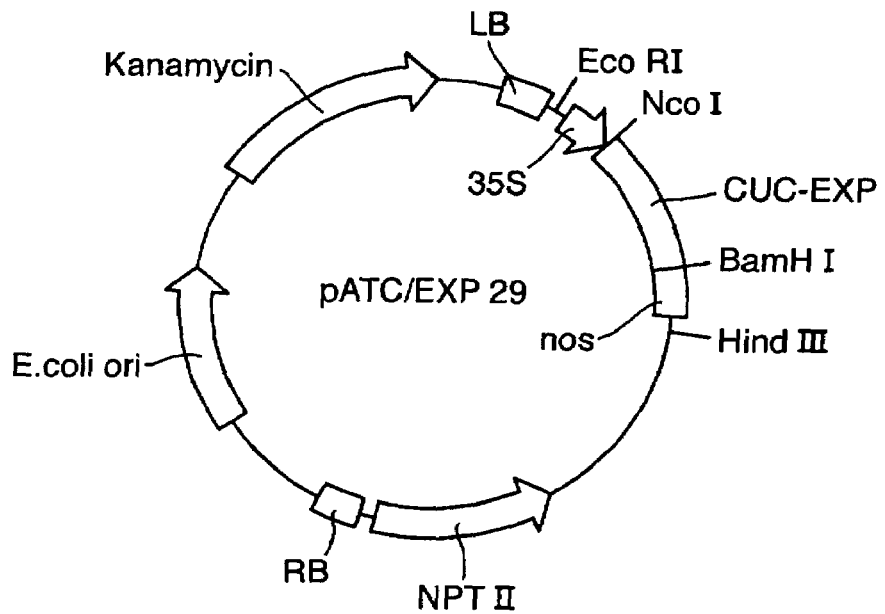
Figure 2:
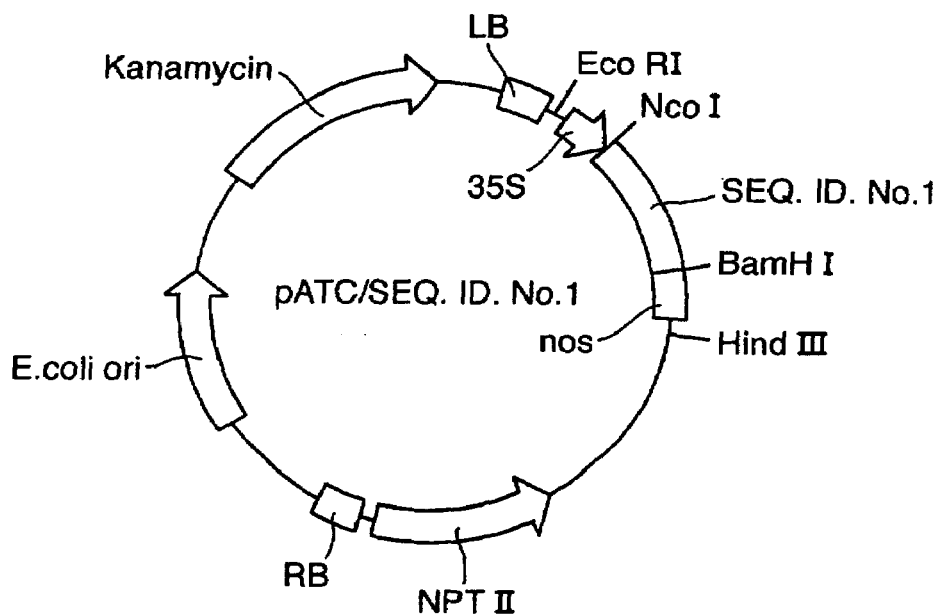

In order that the invention may be easily understood and readily carried into effect, reference will now be made, by way of example, to the following Figures, in which:

FIG. 1a is a diagrammatic representation of the coding sequence for cucumber Ex29 (SEQ. ID. No. 9) cloned between the cauliflower mosaic virus 35S promoter and nos terminator in the vector pDE326;

FIG. 1b is a diagrammatic representation showing the insert from FIG. 1a between the EcoR I and Hind III restriction sites introduced into a modified Ti plasmid pDE 1001 to produce pDE/EXP29, and FIG. 1c is a diagrammatic representation showing the insert from FIG. 1a between the EcoR I and Hind III restriction sites introduced into a modified Ti plasmid p35GUSINT to produce pATC/EXP29; and FIG. 2 is a diagrammatic representation showing an insert containing SEQ. ID. No. 1 between the EcoR I and Hind III restriction sites introduced into a modified Ti plasmid p35GUSINT to produce pATC/SEQ. ID. No.1.

EXAMPLE 1

Isolation of novel expansin sequences from *E. grandis* stem tissue

RNA extraction from cucumber hypocotyls. Seeds of cucumber (*Cucumis sativus* L., cv Burpee pickier, from A.W. Burpee, Westminster, Pa., USA) were sown on water-soaked capillary matting (Fordingbridge Growers Supplies, Arundel, W. Sussex, UK) in plastic trays (35 cm×25 cm×6 cm) and germinated in the dark at 27° C. After 4 days the etiolated seedlings were harvested under green light by excising the upper 20 mm of the hypocotyl into liquid nitrogen and grinding to a fine powder in a pestle and mortar that had previously been chilled at −80° C. Total RNA was extracted in a hot phenol/lithium chloride buffer according to the procedure of Verwoerd et al (1989).

RNA extraction from *Eucalyptus grandis*. *E. grandis* seeds were sown on trays (35 cm×25 cm×6 cm) of Levington's F2 compost (Levington Horticulture Ltd., Ipswich, Suffolk, UK) and germinated in a greenhouse (18–24° C., at a light intensity of approximately 10,000 lux, and 16 hours of daylight). After 8 weeks the seedlings were transferred to individual pots, and then repotted as necessary (approximately every 6–7 weeks) Growing stem tissue was harvested from the last 40–50 mm of branch tips into liquid nitrogen. Immature leaves, usually the youngest two from growing branch tips, were also harvested directly into liquid nitrogen; roots were washed in several bowls of tap water, rinsed with distilled water and then growing tips were excised into liquid nitrogen. RNA was extracted as described by Pawlowski et al (1994) using a protocol especially modified for the extraction of RNA from plants containing high levels of phenolic compounds.

Poly($A^+$) mRNA isolation from total RNA extracted from *E. grandis* stem tissue. Poly($A^+$) mRNA was isolated from total RNA using either push (Stratagene, Cambridge, UK) or spin oligo (dt) columns (Clontech Laboratories, Inc. CA., USA) and following the supplier's instructions and recommendations.

RT-PCR and Sequencing. The nucleic acid sequence of expansins show a considerable extent of divergence. However two regions with a reasonable degree of consensus were identified and used to synthesise two oligonucleotide primers of low complexity (see Table 2).

Total RNA was extracted from young stem tissue and Poly($A^+$) mRNA isolated using oligo(dt) columns as described above. 1 μg of mRNA was used in a PCR experiment (50° C. annealing temperature, 30 cycles, hot start) with the two expansin consensus primers and Taq DNA polymerase (Promega UK Ltd.).

TABLE 2

Sequence of Consensus Expansin Primers

| | Sequence (5'—3') |
|---|---|
| P.1 (SEQ. ID. No. 7) | ATGGIGGIGCNTGYGGNTA |
| P.2 (SEQ. ID. No. 8) | TGCCARTTYTGNCCCCARTT |

Key: Y = C or T, N = A or G or C or T, R = A or G, I = Inosine cDNA Library Construction. For first strand cDNA synthesis 1 μg of mRNA was used in a reaction with 0.15 μg OG1 oligo dt primers and AMV Reverse Transcriptase (9 units/μl, Promega UK Ltd., Southampton, UK).

The library was constructed in the Lambda ZAP II vector (Stratagene, Cambridge, UK), following the supplier's instructions.

Using the methods described, transformed clones were isolated by blue-white colony selection on agar plates following the methods described by the supplier (R&D Systems). Twenty white ("positive") colonies were selected and sequenced. Of these, six were identified as containing sequences that had similarities with other known expansin sequences using a basic BLAST search provided by NCBI. The putative transcripts were all around 450 bps in size (determined by PCR and gel electrophoresis). PCR products were sequenced using a forward primer and the sequences identified as SEQ.ID. Nos. 1–6 were obtained.

EXAMPLE 2

Northern Analysis

Total RNA was isolated from the stem, leaves and roots of *E. grandis* as described above. 6 µg of RNA in 20 µl DEPC $H_2O$ was denatured in a equal volume of denaturing solution (50% formamide, 2×TBE) and run on a standard 1.5% agarose gel at 75 volts for 200 min. RNA from the gel was transferred onto "Zeta-Probe" GT Genomic Tested Blotting Membranes (Biorad Laboratories, California, USA) by capillary transfer. Partial *E. grandis* expansin sequences generated by RT-PCR from stem mRNA (as described above) were used for 32P-random prime labelling and hybridised to the transferred RNA following the membrane supplier's recommended methods (Biorad Laboratories).

EXAMPLE 3

Preparation of Exp29 transformation vector.

RNA extraction from cucumber hypocotyls. Seeds of cucumber (*Cucumis sativus* L., cv Burpee pickier, from A.W. Burpee, Westminster, Pa., USA) were sown on water-soaked capillary matting (Fordingbridge Growers Supplies, Arundel, W. Sussex, UK) in plastic trays (35 cm×25 cm×6 cm) and germinated in the dark at 27° C. After 4 days the etiolated seedlings were harvested under green light by excising the upper 20 mm of the hypocotyl into liquid nitrogen and grinding to a fine powder in a pestle and mortar that had previously been chilled at −80° C. Total RNA was extracted in a hot phenol/lithium chloride buffer according to the procedure of Verwoerd et al (1989).

Vector construction. The coding sequence for cucumber Ex29 (SEQ. ID. No. 9; Genbank Accession No. U30382; known as Cs-EXP1, and Shcherban et al 1995) was generated by RT-PCR and cloned between the Cauliflower Mosaic Virus 35S promoter and nos terminator (see FIG. 1*a*) into pDE326, a vector kindly donated by Dr. Jürgen Denecke of York University. After insertion of the Ex29 expansin sequence the inserts were sequenced to check for correct in frame insertion by sequencing using a primer located within the 35S promoter region.

Inserts containing the 35S promoter, Ex29 sequence and nos terminator were cut between the EcoRI and HindIII restriction sites and inserted into modified Ti plasmids to produce transformation constructs. Two modified Ti plasmids were used: pDE1001 (Denecke et al, 1992 or Shcherban et al 1995) provided by Dr. Jürgen Denecke and p35GUSINT (Vancanneyt et al, 1990). The plasmids produced containing the insert were referred to as pDE/EXP29 (pDE1001+Ex29) (see FIG. 1*b*) and pATC/EXP29 (p35GUSINT+Ex29) (See FIG. 1*c*), acknowledging the source of the plasmids.

Plasmids were transferred into *E. coli* by standard procedures; *E. coli* strains were grown on LB plates (incubated at 37° C. and stored at 4° C.) or in LB medium with the appropriate antibiotic for positive selection.

The constructs were introduced into *Agrobacterium* via direct DNA transformation or by tri-parental mating using the *E. coli* mobilisation function strain HB101 (pRK2013) (Figurski and Helinski 1979).

Two strains of *Agrobacterium tumefaciens* were used. A $C_{5-8}$ strain (C58Cl(pGV2260) Deblaere, R. et al 1985) kindly donated by Dr. Jürgen Denecke, and EHA105 (Hood et al 1993). *Agrobacterium* were grown on LB plates (incubated at 27° C. and stored at 4° C.) or in LB medium with the appropriate antibiotic for positive selection.

International Recognition of the Deposit of Micro-organisms for the purposes of Patent Procedure at the National Collection of Industrial and Marine Bacterial (NCIMB), 23 St Machar Street, Aberdeen, Scotland on 25 Aug. 1998 under Accession No. NCIMB 40968. The micro-organism is *Agrobacterium tumefaciens* strain EHB 105, containing pATC/EXP29. The cDNA for cucumber EX29 (SEQ. ID. No. 9) was inserted into disabled/disarmed pBIN19 (Bevan, 1984) with the 35S cauliflower mosaic virus promoter and nos terminator. The plasmid was then transferred into the *Agrobacterium* strain EHA105. The construct is useful for altering the extension of fibre cell walls.

EXAMPLE 4

Plant Transformation

Young leaves were dissected under sterile conditions, from approximately 4 week old *E. grandis* cultures grown in Magenta boxes (7 cm×7 cm×13 cm) on LS media at 25° C., in a growth room in our tissue culture laboratory and used for *Agrobacterium*-mediated infection (Horsch, Fry, Hoffman, Eichholtz, Rogers, and Fraley 1985). Inoculated tissue was left to co-cultivate for 4d on LS media (plus 20 g/l glucose, 0.7% agarose, 0.01 mM Zeatin a 1 µM NAA) in diffuse light in a growth room, conditions as before. Transformants were selected on 50 mg/l kanamycin and 250 mg/l claforan.

Two constructs for plant transformation were prepared and introduced into two strains of *Agrobacterium*, C58 and EHA105 to produce C58 containing pDE+Ex29, C58 containing PATC+Ex29 and EHA105 containing pATC+Ex29. Each construct-containing strain was used to inoculate 400 leaves dissected from *E. grandis* tissue (on two separate occasions, each time inoculating 200 leaves).

The transformation experiments were repeated with a further 240 leaves, inoculated with EHA105 containing pATC+Ex29 to increase the amount of possible transformants obtainable.

From the original batch of inoculated tissue with EHA105, 25 plants were grown in the greenhouse and the properties of the shoots determined.

The introduction of the expansin coding sequence attached to the 35SCAmV promoter seems to have caused a reduction in the overall height of the plants from a mean control value of 603 mm in the control plants to 546 mm in the transformed plants. Of the survivors of the 25 plants, 4 control and 13 transgenic plants were included in this analysis. This reduction in height is associated with a change in internode length as analysed in the table below. A Chi square analysis of the data in Table 3 indicates that the two populations of plants are significantly different at a value of $P<0.01$.

TABLE 3

| Class of Internode Length (mm) | Number of Internodes in class | | % of internodes in class | |
|---|---|---|---|---|
| | Control | Expansin | Control | Expansin |
| 10 | 1 | 7 | 3 | 6 |
| 20 | 10 | 28 | 28 | 24 |
| 30 | 9 | 28 | 28 | 24 |
| 40 | 4 | 21 | 11 | 18 |
| 50 | 1 | 9 | 3 | 8 |
| 60 | 6 | 12 | 17 | 10 |
| 70 | 2 | 7 | 6 | 6 |
| 80 | 3 | 4 | 8 | 3 |
| >80 | 01 | | | |

From the data it is clear that a modification in the level of expansin activity in the tree can be used to produce a required effect. In order to increase the growth it may be necessary to use down regulation technology, e.g. expression of the reverse or complementary strand of the expansin sequence, or a partial sense expansin sequence, in order to increase the fibre length.

EXAMPLE 5

Sequences SEQ. ID. Nos. 1–6 were each introduced into pATC in both orientations, i.e. antisense and sense orientation, and were used to transform Eucalypts and tobacco using the same methodology as described in Examples 3 and 4. FIG. 2 shows the plasmid pATC/SEQ. ID. No. 1 in sense orientation, as a representative of the plasmids used in the transformation. Any suitable transformation vector can be used.

It was found that the introduction of the novel expansin sequences produced transformed plants different from the control plants.

REFERENCES

Bamber R K (1985) The wood anatomy of Eucalypts and papermaking. Appita 38:210–216

Bevan M W (1984) Binary *Agrobacterium* vectors for plant transformation. Nucl. Acid Res. 12, 871–8721

Boudet A M, Lapierre C+Grima-Pettenati J (1995) Biochemistry and molecular biology of lignification. New Phytol. Tansley rev. 80, 129 203–236

Carpita N C, Gibeaut D M (1993) Structural models of primary cell walls in flowering plants: consistency of molecular structure with the physical properties of the walls during growth. Plant J 3(1): 1–30.

Cho H-T, Kende H (1997) Expansins in deepwater rice internodes. Plant Physiol 113 1137–1143

Cho H-T, Kende H (1997) Expansins and internodal growth of deepwater rice. Plant Physiol 113 1145–1151

Cosgrove D J (1993) Wall extensibility—its nature, measurement and relationship to plant cell growth. New Phytol 124(1):1–23

Cosgrove D J (1996) Plant cell enlargement and the action of expansins. BioEssays 18(7):533–540

Cosgrove D J, Bedinger P, Durachro (1997) Group I allogens of grass pollen as cell wall loosening agents. Proc. Nat. Acad. Sci. USA 94 6559–6564

Deblaere, R. Bytebier, B. De Greve, H., DeBoaeck, F., Schell, J., Van Montagu, M. Leemans, J. (1985) Efficient octopine T-plasmid vectors for *Agrobacterium*-mediated gene transfer to plants. Nucl. Acid. Res., 13, 4777–4788

Denecke J. Rycke R D, Botterman J (1992) Plant and mammalian sorting signals for protein retention in the endoplasmic reticulum contain a conserved epitope. The EMBO Journal 11(6):2345–2355

Figurski D, Helinski D R (1979) Replication of an origin-containing derivative of plasmid RK2 dependent on a plasmid function provided in trans. Proc. Nat. Acad. Sci. USA, 76, 1648–1652

Grima-Pettenati J, Feuillet C, Goffner D, Borderies G, Boudet A M (1993) Molecular cloning and expression of a *Eucalyptus gunnii* clone encoding cinnamyl alcohol dehydrogenase. Plant Mol Bio 21:1085–1095

Hawkins S W, Boudet A M (1994) Purification and characterisation of cinnamyl alcohol dehydogenase isoforms from the periderm of *Eucalyptus gunnii* Hook. Plant Physiol 104:75–84

Herrera-Estrella I, De Block M, Messens E, Hernalsteens JP, Van Montagu M, Schell J (1983) Chimeric genes as dominant selectable markers in plant cells. The EMBO Journal 2:987–995

Hibino T, Chen J-Q, Shibata D+Miguchi T (1994) Nucleotide sequences of a *Eucalyptus botryoides* gene encoding dinnamyl alcohol dehydrogen. Plant Physiol. 104 305–306

Hood E E, Gelvin S B, Melcheri L S, Hoekma A (1993) New *Agrobacterium* helper plasmids for gene transfer to plants. Transgenic Res. 2, 208–218

Horsch R B, Fry J E, Hoffman N L, Eichholtz D, Rogers S G, Fraley RT (1985) A simple and general method for transferring genes into plants. Science 227: 1229–2123

Keller E, Cosgrove D J (1995) Expansins in growing tomato leaves. Plant J 8:795–802

Li Z-C, Durachko D M, Cosgrove D M (1993) An oat coleoptile wall protein that induces wall extension in vitro and that is antigenically related to a similar protein from cucumber hypocotyls. Planta 191:349–356

McQueen-Mason S (1995) Expansins and cell wall expansion. J. Exp. Bot. B46(292):1639–1650

McQueen-Mason S, Cosgrove D J (1993) Cucumber expansins disrupt hydrogen-bonds between cellulose fibers in vitro. Plant Physiol 102(1): 122

McQueen-Mason S, Cosgrove D J (1994) Disruption of hydrogen bonding between plant cell wall polymers by proteins that induce wall extension. Proc Natl Acad Sci USA 91:6574–6578

McQueen-Mason S, Cosgrove D J (1995) Expansin mode of action on cell walls; Analysis of wall hydolysis, stress relaxtion and Binding. Plant Physiol 107:87–100

McQueen-Mason S, Durachko D M, Cosgrove D J (1992) Two endogenous proteins that induce cell wall extension in plants. Plant Cell 4:1425–1433

Miki BLA, Iyer VN (1990) Fundamentals of gene transfer in plants. In: Dennis DT, Turpin DH (eds) Plant Physiology, Biochemistry and Molecular Biology, $1^{st}$ edn. Longman Scientific & Technical Publishers, UK Pawlowski K, Kunze R, De Vries S, Bisseling T (1994) Isolation of total, poly(A) and polysomal RNA from plant tissues. Kluwer Academic Publishers, Belgium Poeydomenge 0, Boudet A M, Grima-Pettenati J (1994) A cDNA encoding S-adenosyl-L-methionin:caffeic acid 3-O-methyltransferase from *Eucalyptus*. Plant Physiol 105:749–750

Ranatunga M S (1964) A study of the fibre lengths of *Eucalyptus grandis* grown in Ceylon. Ceylon For 6:101–112

Shcherban T Y, Shi J, Durachko D M, Guiltinan M J, McQueen-Mason S, Shieh M, Cosgrove D J (1995)

Molecular cloning and sequence analysis of expansins—a highly conserved and multigene family of proteins that mediate cell wall extension in plants. *Proc. Natl. Acad Sci USA* 92:9245–9249

Seth R S (1995) The effect of fibre length and coarseness on the tensile strength of wet webs: a statistical geometry explanation. Tappi J 78 (3) 99–102

Stewart et al (1994)

Vanncanneyt, G, Schmidt, R., O'Connor-Sanchez A, Willmitzer L, Rocha-Sosa M (1990) Construction of an intron-containing marker gene: Splicing of the intron in transgenic plants and its use in monitoring early events in *Agrobacterium*-mediated plant transformation. Mol. Gen. Genet. 220, 245–250

Verhaegen, D, Plomion C (1996) Genetic mapping in *Eucalyptus urophylla* using RAPD markers. Genome 39:1051–1061

Verwoerd T C, Dekker BMM, Hoekema A (1989) A small scale procedure for the rapid isolation of plant RNAs. Nucleic Acids Res. 17(6):2362

Walden R (1994) Cell Culture, Transformation and Gene Technology. In: Lea PJ, Leegood RC (eds) Plant Biochemistry and Molecular Biology, $1^{st}$ edn. John Wiley & Sons Ltd., London Weising K, Schell, J, Kahl G. (1988) Foreign genes in plants: transfer, structure, expression and applications. Ann. Rev. Genet. 22 421–477

What is claimed is:

1. A method of transforming trees to decrease tree height and/or internode length, the method comprising stably incorporating into the plant genome a chimaeric gene comprising a promoter operably linked to a nucleic acid sequence in sense orientation, encoding an expansin capable of modifying tree height and/or internode length, said nucleic acid sequence being the expansin sequence cucumber Ex 29 of SEQ ID NO: 9, or sequences which hybridize thereto under medium stringency conditions, wherein washing is performed with 2×SSC at 65° C., wherein said nucleic acid sequence encodes an expansin and wherein said nucleic acid sequence decreases tree height and/or internode length in plants transformed therewith; and regenerating a tree having an altered genome.

2. The method according to claim 1, wherein said nucleic acid is derived from cucumber.

3. The method according to claim 1, wherein said nucleic acid sequence, is a cDNA sequence or a genomic DNA.

4. A tree transformed according to the method of any of one of claims 1–3.

5. The tree of claim 4, said tree being a eucalypt, aspen, pine, or larch.

6. A seed of a tree transformed according to the method of any one of claims 1–3, said seed comprising said chimaeric gene.

7. The method according to claim 1, wherein said tree is a eucalypt, aspen, pine or larch.

* * * * *

SEQUENCE LISTING

```
<160> NUMBER OF SEQ ID NOS: 10

<210> SEQ ID NO 1
<211> LENGTH: 488
<212> TYPE: DNA
<213> ORGANISM: Eucalyptus grandis

<400> SEQUENCE: 1 atggggggg cttgtgggta tggcaacctg tacagccaag gctatggcac caacactgca      60
gctttgagca ctgccctgtt caacaatggc ctgagctgcg gggcatgtta cgagatgcgg    120
tgcaacgacg accccaggtg gtgcctcccg gggaccatca tggtcacggc aaccaacttt    180
tgccctccca acttggccct ctccaacgac aattgcggct ggtgcaaccc ccctctccag    240
cacttcgata tggccgagcc tgctttcttg cagattgccc agtacaaagc tgggattgtc    300
caggtttcct tcagaagggt tccgtgtgtg aagaaaggag gggtaaggtt caccatcaat    360
gggcactcct acttcaactt ggtgctgatc accaacgtgg gaggtgctgg tgatgtccat    420 tccgttttcca tcaagggctc gaggactggt tggcaagcca tgtcaaggaa ctggggcaaa    480
aactggca                                                              488

<210> SEQ ID NO 2
<211> LENGTH: 475
<212> TYPE: DNA
<213> ORGANISM: Eucalyptus grandis

<400> SEQUENCE: 2 atggggggg catgcgggta tggcaacctg tacagccaag gctatggcac caacactgca      60
gctttgagca ctgccctgtt caacaatggc ctgagctgcg gggcatgtta cgagatgcgg    120
tgcaacgacg accccaggtg gtgcctcccg gggaccatca tggtcacggc aaccaacttt    180
tgccctccca acttggccct ctccaacgac aatggcggct ggtgcaaccc ccctctccag    240
cacttcgata tggccgagcc tgctttcttg cagattgccc agtacaaagc tgggattgtc    300
ccggtttcct tcagaagggt tccgtgtgtg aagaaaggag gggtaaggtt caccatcaat    360
gggcactcct acttcagctg tggtgctgat caccaacgtg ggaggtgctg gtgatgtcca    420 ttccgttttcc atcaagagct cgaggactgg ttggcaagcc atgtcaagga attga         475

<210> SEQ ID NO 3
<211> LENGTH: 494
<212> TYPE: DNA
<213> ORGANISM: Eucalyptus grandis
```

<400> SEQUENCE: 3

```
atggggggg catgtggtta cggggacctt cacagggcca cctatggcaa gtacagtgcc      60
ggcttgagct cgatgctgtt caacagaggg agtacctgcg gggcttgctt cgagctccgg    120
tgcgtcgacc acattttgtg gtgcctccct ggtagcccgt cggtgatcct caccgccacc    180
gacttctgcc ctccgaacta cgggctcgcg gcagattacg gcgggtggtg caacttcccg    240
caggagcact tcgagatgtc ggaggcggcc ttcgccgaga ttgcggtgcg aagggctgat    300
gtggtgccta tccagtacag gagggtgaac tgtctgagaa gcggtggtct gagattcaca    360
ttgagcggaa actctcactt ctttcaggtc ttggtgacga atgtaggcct agatggggag    420
gtgattgcca tgaaaatgaa gggatcgaaa acagggtgga taccgatggc aagaaactgg    480
ggcaaaaact ggca                                                     494
```

<210> SEQ ID NO 4
<211> LENGTH: 437
<212> TYPE: DNA
<213> ORGANISM: Eucalyptus grandis

<400> SEQUENCE: 4

```
atgggttgcc accgggtcct tgatcctttg atggccacgg agtgcacatc ccctgctccg     60
ccgacattgg ttatgagcac gaggttgaaa taagaatggc cgttgacggt gaaccggatc    120
cctccgcttc tcctgcacct cactcttcgg taggccaccg gacgatccc ggccctgtac     180
tgcgcaatgt gctggaagac cggctgggag aggtcgaaat ggagttgagg agggtcgcac    240
caccctcctg gagggcagaa gttggtcgcc gtgaccacaa tggcgcccgg gaggcaccac    300
tgcgggtcgt tcacgcaccg gagctcaaag cacgcgccgc agctcagccc attgttgaac    360
aatgcagtgc tcagtgcagc tgtgtttgtg ccgtacccct tggctgtatag attcccataa    420
ccacacgccc ccccat                                                   437
```

<210> SEQ ID NO 5
<211> LENGTH: 437
<212> TYPE: DNA
<213> ORGANISM: Eucalyptus grandis

<400> SEQUENCE: 5

```
atgggttgcc accgggtcct tgatcctttg atggccacgg agtgcacatc ccctgctccg     60
ccgacattgg ttatgagcac gaggttgaaa taagaatggc cgttgacggt gaaccggatc    120
cctccgcttc tcctgcacct cactcttcgg taggccacag gacgatccc ggccctgtac     180
tgcgcaatgt gctggaagac aggctgggag aggtcgaaat ggagttgagg agggtcgcac    240
caccctcctg gagggcagaa gttggtcgcc gtgacaacaa tggcgcccgg gaggcaccac    300
tgcgggtcgt tcacgcaccg gagctcaaag cacgcgccgc agctcagccc attgttgaac    360
aatgcagtgc tcagtgcagc tgtgtttgtg ccgtacccct tggctgtatag attcccataa    420
ccacacgccc ccccat                                                   437
```

<210> SEQ ID NO 6
<211> LENGTH: 448
<212> TYPE: DNA
<213> ORGANISM: Eucalyptus grandis

<400> SEQUENCE: 6

```
ccttgacatg gtctgccacc ttgtccgcga acccttcacg gcgaccgagt tgacgttgcc      60
tgcgccgccg acgtttgtga cgaggacgag cttgaagtat gagttgccgt tgatggtgaa    120
```

```
ccggatgcct cctctcctcc tgcacgtcac cctcctgtac gcaacgtgga cgatgccggc      180
tcggtacttg gcaatgtgct ggaagacggg ctgggagatg tcgaagtggt gttggggcgg      240
gttgcaccat ccgccggcgt tgtttgggag ggcgttgttt gcgggcaga agtttgtggc       300 ggtgacgacg atggagccgc ccaggcacca ctttccgtcg ttcacgcacc ggatctcgaa      360
gcacgacccc cagctcagcc cgttttttaa cagcgccgtg ctcagcgccg ccgtgttcgt      420
accgtagccc tggctgtaca ggttgccg                                         448
```

```
<210> SEQ ID NO 7
<211> LENGTH: 19
<212> TYPE: DNA
<213> ORGANISM: Eucalyptus grandis
<220> FEATURE:
<221> NAME/KEY: misc_feature
<222> LOCATION: (8)..(8)
<223> OTHER INFORMATION: n represents inosine
<220> FEATURE:
<221> NAME/KEY: misc_feature
<222> LOCATION: (5)..(5)
<223> OTHER INFORMATION: n represents inosine
<220> FEATURE:
<221> NAME/KEY: misc_feature
<222> LOCATION: (11)..(11)
<223> OTHER INFORMATION: n represents a, g, t, or c
<220> FEATURE:
<221> NAME/KEY: misc_feature
<222> LOCATION: (17)..(17)
<223> OTHER INFORMATION: n represents a, g, t, or c

<400> SEQUENCE: 7
atggnggngc ntgtggnta                                                    19
```

```
<210> SEQ ID NO 8
<211> LENGTH: 20
<212> TYPE: DNA
<213> ORGANISM: Eucalyptus grandis
<220> FEATURE:
<221> NAME/KEY: misc_feature
<222> LOCATION: (12)..(12)
<223> OTHER INFORMATION: n = a, g, t, or c
<220> FEATURE:
<221> NAME/KEY: misc_feature
<222> LOCATION: (9)..(9)
<223> OTHER INFORMATION: y = t or c
<220> FEATURE:
<221> NAME/KEY: misc_feature
<222> LOCATION: (6)..(6)
<223> OTHER INFORMATION: r = a or g
<220> FEATURE:
<221> NAME/KEY: misc_feature
<222> LOCATION: (18)..(18)
<223> OTHER INFORMATION: r = a or g

<400> SEQUENCE: 8
tgccarttyt gnccccartt                                                   20
```

```
<210> SEQ ID NO 9
<211> LENGTH: 992
<212> TYPE: DNA
<213> ORGANISM: Cucumis sativus
<220> FEATURE:
<221> NAME/KEY: CDS
<222> LOCATION: (154)..(906)

<400> SEQUENCE: 9
gaataattaa caaacattgc cactaattaa tctcatttat taaacacatt tcttttttcgc     60 taatctcccc tttcttcccc ctcttctctt ctaaacccac aaaacaaacc ccactttttct    120
```

-continued

```
tcacaaacta ttttcaaata taaacccatt ctt atg gct ttt tct tac tca ccc      174
                                    Met Ala Phe Ser Tyr Ser Pro
                                      1               5 ttc tcc tct ctc ttt ctt ctt cct ttc ttc ttt gtc ttc acc ttc gct      222
Phe Ser Ser Leu Phe Leu Leu Pro Phe Phe Phe Val Phe Thr Phe Ala
            10                  15                  20 gac tac ggt ggc tgg cag agc ggc cac gcc acc ttt tat ggt ggt ggt      270
Asp Tyr Gly Gly Trp Gln Ser Gly His Ala Thr Phe Tyr Gly Gly Gly
        25                  30                  35 gac gca tct ggc acc atg ggt gga gct tgt ggg tat ggg aat tta tac      318
Asp Ala Ser Gly Thr Met Gly Gly Ala Cys Gly Tyr Gly Asn Leu Tyr
 40                  45                  50                  55 agc caa ggg tat ggc acg aac acg gtg gcg ctg agc act gcg cta ttt      366
Ser Gln Gly Tyr Gly Thr Asn Thr Val Ala Leu Ser Thr Ala Leu Phe
                60                  65                  70 aac aat gga tta agt tgt ggt gct tgc ttc gaa atg act tgt aca aac      414
Asn Asn Gly Leu Ser Cys Gly Ala Cys Phe Glu Met Thr Cys Thr Asn
            75                  80                  85 gac cct aaa tgg tgc ctt ccg gga act att agg gtc act gcc acc aac      462
Asp Pro Lys Trp Cys Leu Pro Gly Thr Ile Arg Val Thr Ala Thr Asn
        90                  95                 100 ttt tgc cct cct aac ttt gct ctc cct aac aac aat ggt gga tgg tgc      510
Phe Cys Pro Pro Asn Phe Ala Leu Pro Asn Asn Asn Gly Gly Trp Cys
105                 110                 115 aac cct cct ctc caa cac ttc gac atg gct gag cct gcc ttc ctt caa      558
Asn Pro Pro Leu Gln His Phe Asp Met Ala Glu Pro Ala Phe Leu Gln
120                 125                 130                 135 atc gct caa tac cga gct ggt atc gtc ccc gtc tcc ttt cgt agg gta      606
Ile Ala Gln Tyr Arg Ala Gly Ile Val Pro Val Ser Phe Arg Arg Val
                140                 145                 150 cca tgt atg aag aaa ggt gga gtg agg ttt aca atc aat ggc cac tca      654
Pro Cys Met Lys Lys Gly Gly Val Arg Phe Thr Ile Asn Gly His Ser
            155                 160                 165 tac ttc aac ctc gtt ttg atc aca aac gtc ggt ggc gca ggc gac gtc      702
Tyr Phe Asn Leu Val Leu Ile Thr Asn Val Gly Gly Ala Gly Asp Val
        170                 175                 180 cac tct gtg tcg ata aag ggg tct cga act gga tgg caa tcc atg tct      750
His Ser Val Ser Ile Lys Gly Ser Arg Thr Gly Trp Gln Ser Met Ser
185                 190                 195 aga aat tgg ggc caa aac tgg caa agc aac aac tat ctc aat ggc caa      798
Arg Asn Trp Gly Gln Asn Trp Gln Ser Asn Asn Tyr Leu Asn Gly Gln
200                 205                 210                 215 ggc ctt tcc ttt caa gtc act ctt agt gat ggt cgc act ctc act gcc      846
Gly Leu Ser Phe Gln Val Thr Leu Ser Asp Gly Arg Thr Leu Thr Ala
                220                 225                 230 tat aat ctc gtt cct tcc aat tgg caa ttt ggc caa acc tat gaa ggc      894
Tyr Asn Leu Val Pro Ser Asn Trp Gln Phe Gly Gln Thr Tyr Glu Gly
            235                 240                 245 cct caa ttc taa accatatcag ccacactgct atgactacta ctacttcaca          946
Pro Gln Phe
        250 aaacaaaaca cacaaaacaa acaaacaaca acaaaacgcg aacgac                   992
```

<210> SEQ ID NO 10
<211> LENGTH: 250
<212> TYPE: PRT
<213> ORGANISM: Cucumis sativus

<400> SEQUENCE: 10

-continued

```
Met Ala Phe Ser Tyr Ser Pro Phe Ser Ser Leu Phe Leu Leu Pro Phe
 1           5               10                  15

Phe Phe Val Phe Thr Phe Ala Asp Tyr Gly Gly Trp Gln Ser Gly His
            20              25                  30

Ala Thr Phe Tyr Gly Gly Gly Asp Ala Ser Gly Thr Met Gly Gly Ala
            35              40                  45

Cys Gly Tyr Gly Asn Leu Tyr Ser Gln Gly Tyr Gly Thr Asn Thr Val
 50                  55                  60

Ala Leu Ser Thr Ala Leu Phe Asn Asn Gly Leu Ser Cys Gly Ala Cys
 65                  70              75                      80

Phe Glu Met Thr Cys Thr Asn Asp Pro Lys Trp Cys Leu Pro Gly Thr
                85              90                  95

Ile Arg Val Thr Ala Thr Asn Phe Cys Pro Pro Asn Phe Ala Leu Pro
            100             105             110

Asn Asn Asn Gly Gly Trp Cys Asn Pro Pro Leu Gln His Phe Asp Met
            115             120             125

Ala Glu Pro Ala Phe Leu Gln Ile Ala Gln Tyr Arg Ala Gly Ile Val
        130             135             140

Pro Val Ser Phe Arg Arg Val Pro Cys Met Lys Lys Gly Gly Val Arg
145                 150             155                     160

Phe Thr Ile Asn Gly His Ser Tyr Phe Asn Leu Val Leu Ile Thr Asn
                165             170                 175

Val Gly Gly Ala Gly Asp Val His Ser Val Ser Ile Lys Gly Ser Arg
                180             185                 190

Thr Gly Trp Gln Ser Met Ser Arg Asn Trp Gly Gln Asn Trp Gln Ser
            195             200                 205

Asn Asn Tyr Leu Asn Gly Gln Gly Leu Ser Phe Gln Val Thr Leu Ser
    210                 215             220

Asp Gly Arg Thr Leu Thr Ala Tyr Asn Leu Val Pro Ser Asn Trp Gln
225                 230             235                 240

Phe Gly Gln Thr Tyr Glu Gly Pro Gln Phe
                245             250
```